United States Patent [19]

Rosen et al.

[11] Patent Number: 5,231,998
[45] Date of Patent: Aug. 3, 1993

[54] WHOLE-ARM ORTHOSIS FOR STEADYING LIMB MOTION

[75] Inventors: Michael J. Rosen, Arlington, Mass.; Ivan J. Baiges, Mayaguez, P.R.

[73] Assignee: Massachusetts Institute of Technology, Cambridge, Mass.

[21] Appl. No.: 543,214

[22] Filed: Jun. 25, 1990

[51] Int. Cl.⁵ ................................ A61F 5/37
[52] U.S. Cl. .................. 128/878; 128/24 R; 128/845; 602/19; 602/20
[58] Field of Search .............. 602/19, 20; 128/24 R, 128/25 R, 845, 846, 878, 879; 434/258; 623/24

[56] References Cited

U.S. PATENT DOCUMENTS

| | | | |
|---|---|---|---|
| 4,078,670 | 3/1978 | Francois et al. | 623/24 X |
| 4,689,449 | 8/1987 | Rosen . | |
| 5,020,790 | 6/1991 | Beard et al. | 623/24 X |
| 5,107,080 | 4/1992 | Rosen . | |

OTHER PUBLICATIONS

"Suppression of Intention Tremor by Mechanical Loading", M. S. Thesis, M.I.T. Department of Mechanical Engineering, Feb. 1979.

"The Use of a Mechanically Damped Joystick as a Means of Reducing Intention Tremor" by Kathleen Marie Laffey, B. S. Thesis, M.I.T. (May '85) Mech. Engrg.

"Damped Arm Restraint for Tremor Patients" by Susan Russell Stapleton, B. S. Thesis, M.I.T. (May 1982) Mech. Engrg.

"Development of a Whole-Arm Orthosis for Abnormal Intentional Tremor Suppression" by Ivan Jose Baiges Valentin, M. S. Thesis, M.I.T. (Aug. 1989), Mech. Engrg.

"Viscously Damped Joystick for Proportional Control by Tremor Patients" by Steven Beringhouse, M. S. Thesis, M.I.T. (Aug. 1988).

"A Virtual Environment System for the Study of Human Arm Tremor" by Bernard Dov Adelstein, Ph.D. Thesis, M.I.T. (Jun. 1989).

"Goal Definition Spreadsheet for the Design of a Damped Wrist Orthosis" by David T. Wimberly, Jr., B.S. Thesis, M.I.T. (Jun. 1989) Mech. Engrg.

"Peripheral Mechanical Loading and the Mechanism of Abnormal Intention Tremor" by Bernard Dov Adelstein, M.S. Thesis, M.I.T. (Jul. 1981) Mech. Engrg.

U.S. application Ser. No. 444,500, filed Dec. 1, 1989, "Multiple Degree of Freedom Damped Hand Controls" by Rosen.

"A High Performance Two Degree-of-Freedom Kinesthetic Interface" by Adelstein et al., *Proceedings of the Eng. Foundation Conf. on Human Machine Interfaces for Teleoperators and Virtual Environments*, Santa Barbara, Calif., Mar. 1990.

"Evaluation of a Damped Joystick for People Disabled by Intention Tremor" by Beringhouse et al., *RESNA 12th Annual Conference*, New Orleans, La. 1989, pp. 41, 42.

"A High Performance Two Degree-of-Freedom Kinesthetic Interface" by Adelstein et al., *Poster Abstract, Engineering Foundation Conference*, Santa Barbara, Calif., Mar. 1990.

"Suppression of Abnormal Intention Tremor by Application of Viscous Damping" by Rosen et al., 4th Congress of I.S.E.K., Boston, Mass., 1979.

"A Damped Joystick: Adaptive Control for the Tremor-Disabled" by Rosen et al., *2nd Interagency Conference on Rehabilitation Engineering*, Atlanta, Ga., Aug. 1979.

(List continued on next page.)

Primary Examiner—Robert A. Hafer
Assistant Examiner—Gregory M. Stone
Attorney, Agent, or Firm—Hamilton, Brook, Smith & Reynolds

[57] ABSTRACT

A whole arm orthosis with plural degrees of freedom dampens limb tremors. A linkage mechanism permits movement of the forearm in a horizontal plane, as well as tilting of the forearm out of the horizontal plane. A sensor coupled to the joints of the linkage mechanism detects the angular velocity of rotation. A brake applies resistive torque to the joints in accordance with the angular velocity of rotation.

20 Claims, 3 Drawing Sheets

U.S. PATENT DOCUMENTS

"Attenuation of Abnormal Intention Tremor Following Viscous Exercise: Work in Progress" by Rosen et al., *Proceedings of Int'l Conf. on Rehab. Engrg.*, Toronto 1989, pp. 202, 203.

"Hypothetical Diagnostic Classification of Tremor According to Variation with Mechanical Loads" by Rosen et al., *Fourth Annual Conf. on Rehab. Engineering*, Washington, D.C. 1981.

"The Effect of Mechanical Inpedance on Abnormal Intention Tremor" by Adelstein et al., *Proceedings of the Ninth Northeast Conference on Bioengineering*, Rutgers University, New Brunswick, N.J. 1981.

"Modification of Spastic Gait Through Mechanical Damping" by Rosen et al., *IFAC Control Aspects of Prosthetics and Orthotics* 1982.

"Objective Correlates of Clinical Judgement of Tremor Severity" by Pardoel et al., *6th Annual Conference on Rehabilitation Engineering*, San Diego, Calif. 1983.

"Design of a Two-Degree-of-Freedom Manipulandum for Tremor Research" by Rosen et al., *IEEE Frontiers of Engineering and Computing in Health Care—1984*, pp. 47-51.

"Modification of Spastic Gait Through Mechanical Damping" by Maki et al., *J. Biomechanics*, vol. 18, No. 6, pp. 431-443.

"Tremor Mechanism Identification by Peripheral Limb Loading" by Adelstein et al., *Proceedings of 8th Annual Conference of IEEE EMB Society*, Forth Worth, Tex., Nov. 1986.

"Evaluating manual control devices for those with tremor disability" by Riley et al., *J. Rehab. Res. & Dev.*, vol. 24, No. 2, pp. 99-110, 1987.

"Differential Diagnosis of Pathological Tremors According to Mechanical Load Response" by Adelstein et al., *RESNA 10th Annual Conference*, San Jose, Calif. 1987.

"A Two-Degree-of-Freedom Loading Manipulation for the Study of Human Arm Dynamics" by Adelstein et al., 1987 *Advances in Bioengineering*, pp. 111-112.

"A Second-Generation Joystick for People Disabled by Tremor," by Hendriks et al., RESNA 14th Annual Conf., Kansas City, Mo. 1991.

U.S. patent application Ser. No. 07/648,733 filed on Jan. 13, 1991.

WHOLE-ARM ORTHOSIS FOR STEADYING LIMB MOTION

TECHNICAL FIELD

This invention is in the field of orthotics.

BACKGROUND ART

The presence of random involuntary limb movement superimposed on purposeful limb movement is an abnormal condition that afflicts hundreds of thousands of patients suffering from a variety of diseases. Many tremor patients are disabled by these involuntary movements due to the fact that the amplitude of these movements is large enough to degrade or obscure voluntary movement attempted by the patient. Cerebral palsy patients suffering from athetosis may also be disabled by their involuntary limb movement. Chorea is another such condition.

In each of these cases, patients typically try to overcome the disability imposed by the involuntary movements of a particular limb either by steadying its motion using an unafflicted limb, by jamming the afflicted limb against the body so as to restrict its vibration, or even by having another person grasp the limb to steady its motion. Drug therapies and surgery have been attempted with limited effectiveness and considerable risk for the patient.

However, in the past ten years or so, a small number of assistive devices, i.e., orthoses, have been developed experimentally that are meant to selectively suppress the random involuntary movements. These devices are based on the experimental observation that significant reduction of the involuntary movements can be achieved by the application of viscous damping to the afflicted limb or body segment.

One such device is a one degree-of-freedom (DOF) orthosis with an electronically-controlled magnetic particle brake used to retard limb motion (See Dunfee, D. E., "Suppression of Intention Tremor by Mechanical Loading", M.S. Thesis, M.I.T. Department of Mechanical Engineering, February 1979). This device, meant primarily for conducting experiments at the wrist, prevents the patient from performing whole-arm functional activities, since limb motion is rigidly constrained in the remaining DOF's.

Another prior art device is a 2 degree-of-freedom joystick meant to serve as a control interface to electrical devices (such as powered wheelchairs) while applying a resistive load to the limb. This system cannot be used for whole-arm movements and is not meant as a general purpose functional orthosis.

SUMMARY OF THE INVENTION

The orthosis of the present invention is a four-DOF orthosis which allows the patient to move the midpoint of the forearm in a horizontal plane (accommodating the position and the orientation of the forearm in that plane) via the rotation of certain joints in the orthosis linkage, and to tilt the forearm out of this plane via the rotation of another joint. This motion is sufficient to allow performance of a variety of seated functional arm activities over a useful range of motion. The patient's arm motion is resisted, or damped, in the planar translation and tilt DOFs by three magnetic particle brakes where the magnitude of each damping torque is computer controlled. It may, for example, be kept proportional to a joint's angular velocity as measured by the processed output of a potentiometer or other transducer coupled to the output shafts of these joints and to the orthosis base.

The planar transmission linkage of the orthosis is a four-bar parallelogram linkage, coupled to mechanical ground at one revolute joint. The linkage achieves a high stiffness-to-mass ratio by means of choice of material and high cross-sectional moment of inertia. The rotation of this parallelogram linkage and its change in shape gives the rise to its horizontal planar motion.

The particle brakes and position sensors are located at the base joint of the parallelogram linkage. Note that it was possible to fix both brakes for the planar DOFs on the orthosis base because the four-bar linkage acts as a transmission. This choice greatly reduces the effective inertia felt at the end point by the patient by making it unnecessary to mount one at the brakes on the moving linkage. The base of the orthosis is attached via a mounting plate to some external surface for support, such as a wheelchair.

The link most distant from the base is L-shaped so as to avoid interference with the patient's elbow during tilt movements. Its distal end is coupled through a revolute joint about a vertical axis to a limb coupler assembly. This incorporates a limb coupling cuff, or splint, a magnetic particle brake, and a potentiometer. A horizontal revolute joint in this limb coupler assembly has a horizontal axis and provides a third damped DOF. The vertical axis accommodates orientation changes of the forearm in the horizontal plane (which are generally coupled to forearm position by human anatomy if the shoulder is kept stationary).

DETAILED DESCRIPTION OF THE INVENTION

Figure 1:
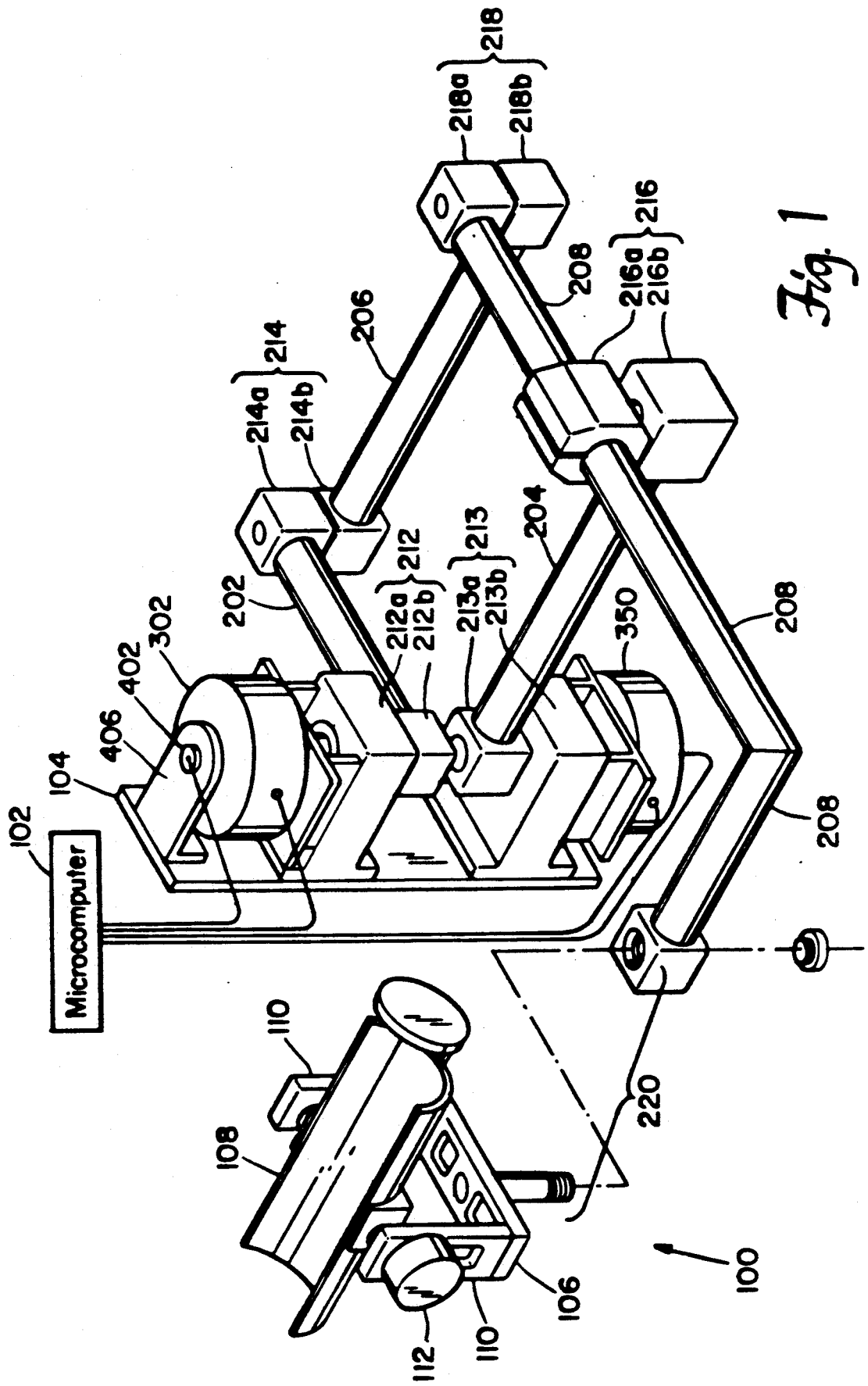
FIG. 1 is a simplified mechanical drawing of the orthosis of the invention.

The orthosis is now described in connection with FIGS. 1–4. FIG. 1 shows the apparatus of the orthosis, which is comprised of a planar transmission linkage (consisting of links and joints), particle brakes, angle sensors, a limb coupler assembly, and a mounting plate. Each of these components is described in the following sections. The orthosis is used in conjunction with a microcomputer 102, which is used to obtain velocity measurements from the measured positions and control the brakes of the orthosis in response to these measurements. Finally, the mounting plate 104 of the orthosis is attached to some external surface for support, such as a wheelchair.

I. Planar Transmission Linkage

In FIG. 1, the planar transmission linkage is seen to comprise a set of tubes, or 'links' 202–208, joined together by revolute joints 212–218 that allow rotation of the links with respect to one another. Since the links are aluminum or composite and have large cross-sectional moment of inertia, a high stiffness-to-mass ratio is achieved. This ratio determines the amount of damping that can be applied by the brakes before link elasticity becomes significant relative to damping. The high stiffness characterizing the links is also desired to rigidly restrain the user's motions in the vertical directions.

The planar transmission linkage permits motion at the limb coupling assembly 100 in 2 DOFs and converts torques produced by the two fixed brakes 302 and 350 to forces at the coupling assembly. The rotation about joint 220 allows changes in angle in the horizontal plane of the limb coupling assembly. The rotation of joint 222 allows the forearm (in the limb coupling cuff 108 of FIG. 1) to tilt out of the horizontal plane.

The planar transmission linkage in the preferred embodiment consists of four links 202–208 in the preferred embodiment arranged as a parallelogram with link 208 extended in an L shape. Link 208 is rigidly connected to the upper half 216a of joint 216, while link 204 is rigidly connected to the lower half 216b of joint 216. The relative rotation of the upper and lower halves of joint 216, i.e., the rotation of joint 216, thereby causes links 204 and 208 to rotate relative to each other. Similarly, links 208 and 206 and links 202 and 206 are rigidly connected to the upper and lower halves of joints 218 and 214, respectively.

In addition, link 202 is rigidly connected to the lower half 212b of joint 212, which rotates relative to the upper half 212a. Likewise, link 204 is rigidly connected to the upper half 213a of joint 213, which rotates relative to the lower half 213b. Hence, equal rotations of joints 212 and 213 cause the entire planar transmission linkage to rotate relative to the mounting plate 104. Rotations of these two joints relative to each other cause changes in the shape of the linkage.

II. Coupling of Planar Transmission Linkage to Mounting Plate

Figure 3:
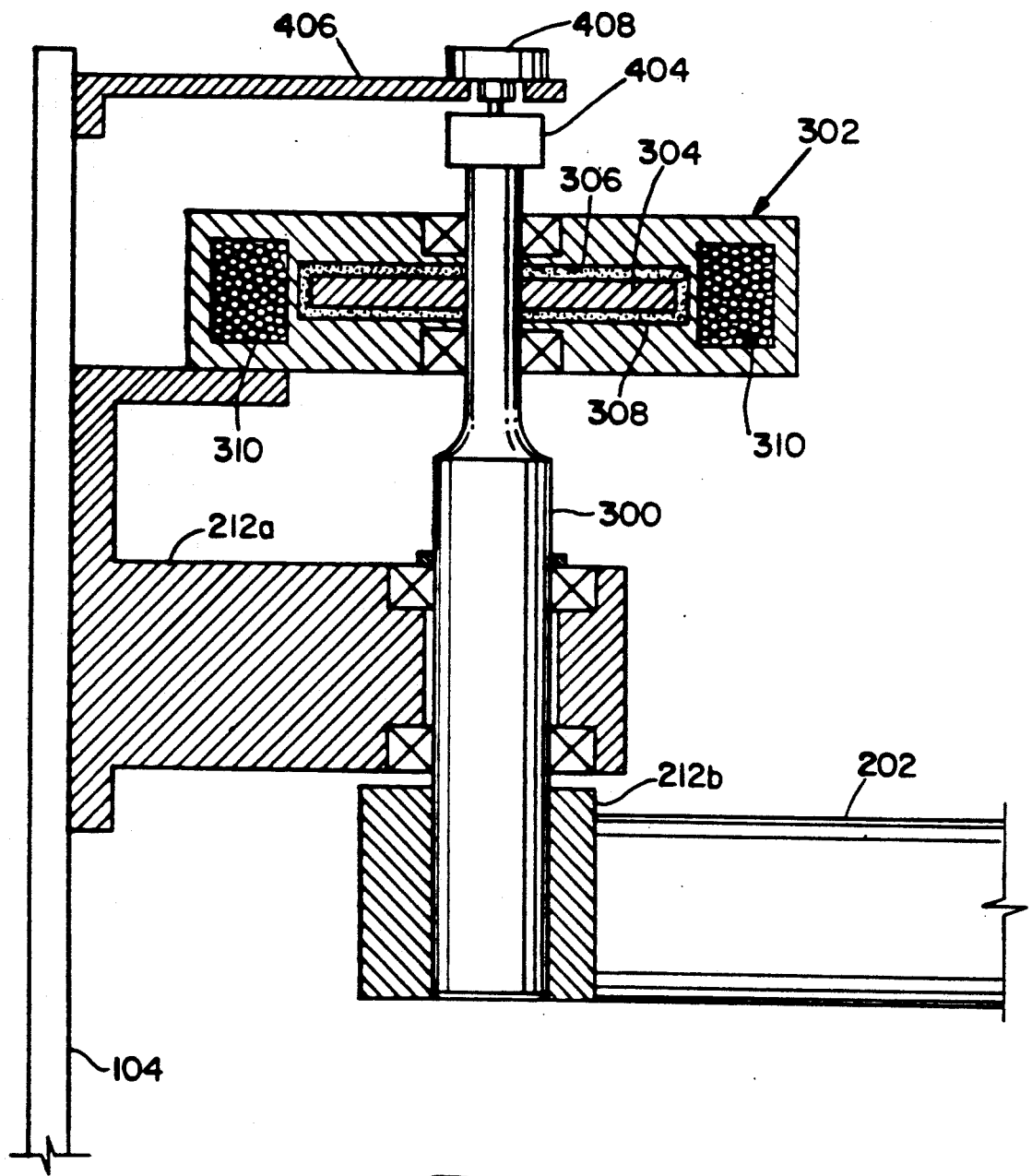
FIG. 3 is a diagram of the assembly coupling link 202 of FIG. 1 to the mounting plate, including a particle brake and potentiometer.

Each of links 202 and 204 is coupled to an assembly comprising an output shaft, a bearing block, a position sensor, and a magnetic particle brake. As shown in FIG. 3, link 202 is rigidly coupled to the lower half 212b of joint 212, which is in turn rigidly coupled to output shaft 300. Similarly, the upper half 212a of joint 212, i.e., bearing block 212a, is rigidly connected to mounting plate 104. The rotation of link 202 relative to the mounting plate 104 causes rotation of the output shaft 300 relative to the bearing block 212a.

This rotational motion (i.e., the amount that joint 212 has been rotated) is measured by an angle sensor consisting, for example, of a potentiometer 402 or shaft encoder. The position sensor indicates the angle $\alpha$ (see FIG. 2) of link 202 relative to the mounting plate 104. As joint 212 of FIG. 3 rotates, the shaft of the potentiometer, which is coupled by flexible coupling 404 to the output shaft 300, rotates relative to the potentiometer body 408, which is fixed to the mounting plate 104 by bracket 406. This action varies a measurable electrical signal. The microcomputer 102 of FIG. 1 differentiates this signal to obtain a measurement of the angular velocity $\dot{\alpha}$ of the joint (i.e., how fast the angle $\alpha$ between link 202 and the mounting plate 104 is changing).

Referring back to FIG. 3, the rotational motion of joint 212 is resisted in a controlled manner by magnetic particle brake 302 which is supported on plate 104 with sufficient compliance to account for minor shaft misalignment. The particle brake consists of a disk 304 that is attached to the output shaft 300 of the joint 212. The disk 304 resides in a cylindrical cavity 306 larger than the disk. Powdered magnetic particles 308 are contained in the gap surrounding the disk. A coil of wire 310 is wound around the cylindrical cavity.

When an electrical current travels through the coil 310, a magnetic field parallel to the cylindrical axis of the disk 304 is produced in the cavity 306. The magnetic particles 308 in the gap align to form what resemble 'chains' in response to the applied current, and these chains of particles 308 apply a torque in opposition to the rotation of the disk 304 rotating along with the output shaft 300 to which it is attached, thereby resisting the motion of the output shaft 300. The particle brake 302 produces a resistive torque approximately proportional to the applied coil current so that the braking torque may be modulated by varying the applied coil current. In the present embodiment, the applied coil current is varied so that it is proportional to the calculated angular velocity measurement of a joint, in this case, joint 216. Hence, the damping force is proportional to the joint velocity.

A measure of the rotation of joint 216 is not directly available, however, since no potentiometer is connected to it. Instead, as will be shown below, the difference between the two angles $\alpha$ and $\beta$ that are measured by potentiometers provides the desired measurement. It should be noted that different embodiments can incorporate more complex control equations relating brake currents to angular velocities and to angles themselves (since it may be desirable to vary the damping for different human arm locations).

First, the assembly for link 204 is described. The assembly coupling link 204 to the mounting plate 104, including the position sensor and magnetic particle brake for joint 213, is exactly the same as that described for link 202 above, with the exception that the entire assembly for link 204 is inverted. Hence, a figure for the assembly corresponding to link 204 is not shown. Instead, reference numerals are directed to FIG. 1. Here, link 204 is rigidly coupled to the upper half 213a of joint 213, which is in turn rigidly coupled to an output shaft similar to output shaft 300 of FIG. 3. Similarly, the lower half 213b of joint 213, i.e., joint base 213b, is rigidly connected to mounting plate 104. The rotation of the output shaft relative to the joint base 213b causes rotation of link 204 relative to the mounting plate 104.

This rotational motion (i.e., the amount that joint 213 has been rotated) is measured by an angle sensor 452 consisting of a potentiometer, or other transducer as for 402. This angle sensor transduces the angle $\beta$ by which link 204 has been rotated relative to the mounting plate 104. Once again, the microcomputer 102 of FIG. 1 differentiates the angle $\beta$ to obtain an approximation of the angular velocity $\dot{\beta}$ of the joint (i.e., how fast the angle $\beta$ between link 204 and the mounting plate 104 is changing).

Just as for joint 212, the rotational motion of joint 213 is resisted in a controlled manner by a magnetic particle brake 350. The coil current applied to the brake 350 is varied so that it is proportional to the angular velocity measurement $\dot{\beta}$ of joint 123. Hence, the damping force is proportional to the joint velocity.

Figure 2:
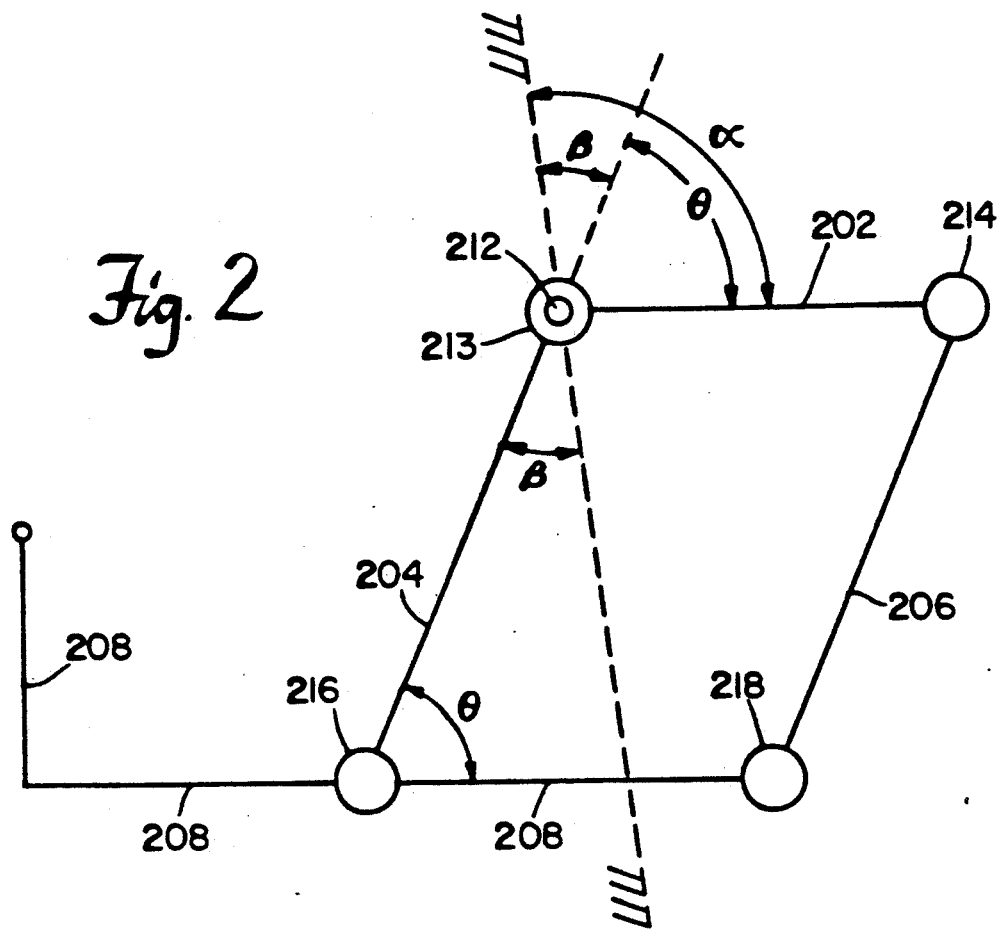
FIG. 2 is a schematic representation of the planar transmission linkage of the orthosis of FIG. 1.
Figure 4:
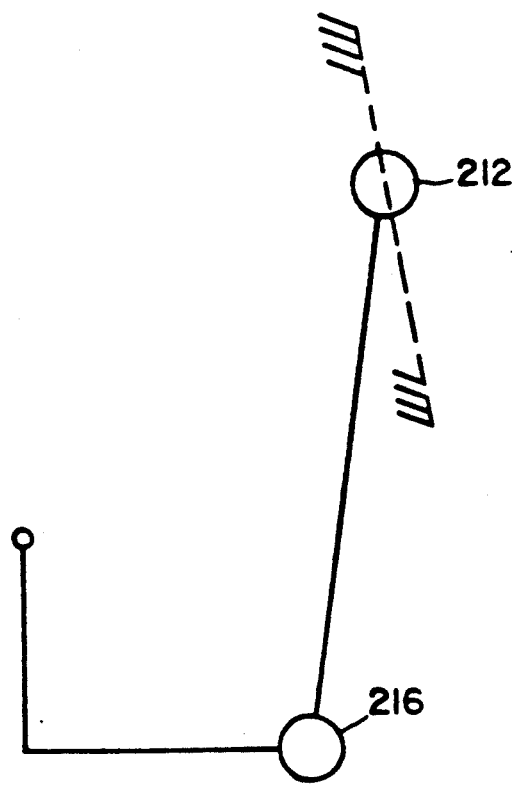
FIG. 4 is a schematic depicting an alternate inferior linkage design having a greater effective inertia at the endpoint.

FIG. 2 illustrates the manner in which the angles $\alpha$ and $\beta$ measured by potentiometers yield a measurement of the angle $\theta$, i.e., the amount that joint 216 has been rotated. (Recall that $\theta$, or more accurately, $\dot{\theta}$, is a quantity that determines the damping force of particle brake 302.) As seen in the figure, $\alpha$ is the angle subtended by link 202 relative to some mechanical ground, which is represented by a dotted line 222 and corresponds to the mounting plate 104. Similarly, $\beta$ is the angle subtended by link 204 relative to the same mechanical ground. From the geometry in the figure, it is evident that $\dot{\theta} = \dot{\alpha} - \dot{\beta}$. Hence, obtaining measurements of $\dot{\alpha}$ and $\dot{\beta}$ and then damping joint 212 as a function of the difference is equivalent to obtaining measurements of $\dot{\theta}$ and damping joint 216 directly.

It is the planar transmission linkage which, through the geometry of FIG. 2, permits the placement of particle brake 302 and related components at the orthosis base instead of at joint 216. The placement of both brakes fixed on the base plate has the effect of reducing the effective endpoint inertia felt by the patient that would be present in the alternative arrangement of FIG. 4. In particular, while the FIG. 4 device would have the same DOF's as the present device as well as the advantage of a simpler geometry in which the brakes for joints 212 and 216 are located at their respective joints, the considerable extra mass at joint 216 contributed by its brake would significantly increase the endpoint inertia felt by the user.

Alternate embodiments of the planar transmission linkage could employ pulleys or sprockets for example, coupled to joints 216a and 212b and joined by belts, cables, or chains. These approaches would be likely to exhibit friction, backlash and compliance in excess of the preferred embodiment, however.

III. Coupling of the Planar Transmission Linkage to Limb Coupling Assembly

Referring back to FIG. 1, the end of link 208 that is not coupled to joint 216 couples the planar transmission linkage to the limb coupler cuff assembly. One embodiment comprises a U-shaped support 106 with bearings aligned on an axis near the top of each vertical member 110 of the support. These accommodate two coaxial shafts (not shown) rigidly coupled to a limb coupler trough 108 or cuff in which the forearm is held. The shaft is also rigidly coupled to the shaft of a third potentiometer or other sensor (mounted on the vertical member which does not support the brake) used to provide a measure of the angle of the limb coupler cuff relative to the support 106. Finally, the rotational motion of the cuff about this axis is damped by magnetic particle brake 112, whose rotation disk is rigidly coupled to the shaft and whose housing is coupled to vertical support 110. As before, the damping force is proportional to the angular velocity of the output shaft, which is obtained by microcomputer 102 via differentiation of the sensor signal.

The limb coupler cuff 108 itself acts as the physical interface between the human limb (here, the forearm) and the orthosis, and has the function of transferring the loads form the orthosis to the limb. The goal of the cuff is to provide the stiffest practical connection between the orthosis and the limb, so that control of the orthosis over the limb is maximized without substantially sacrificing user comfort. The cuff can have several configurations, including a simple trough or a splint which embraces parts of the forearm, wrist, thumb and hand.

Utility

The orthosis of the invention is motivated primarily by the need to overcome the disability posed by involuntary movements due to abnormal condition, such as tremor, athetosis, and chorea. However, in a general sense, the orthosis can be used in any application in which the motion of a limb is to be steadied, and might include those in which delicate tasks are to be carried out in a vibrating environment. Another possible application might be that in which the orthosis is used to perform tasks that are highly sensitive to involuntary limb vibrations and require extreme manual dexterity (e.g., surgical tasks).

Equivalents

This completes the description of the preferred embodiment of the invention. Those skilled in the art may recognize other equivalents to the specific embodiments described herein, which equivalents are intended to be encompassed by the claims attached hereto.

We claim:
1. A system to restrain limb motion comprising:
   a) an N degree of freedom linkage mechanism having a plurality of rotational joints for coupling said limb thereto which permit rotation of said limb about N different axes where N is at least two;
   b) sensor means coupled to a predetermined subset of said joints for generating a velocity signal proportional to the angular velocity of said rotation; and
   c) braking means responsive to the velocity signal for applying a resistive torque to a predetermined subset of said joints wherein said torque is a function of the angular velocity of said rotation.
2. The system of claim 1 wherein N is at least 3.
3. The system of claim 1 wherein the linkage mechanism is a five-bar linkage.
4. The system of claim 3 wherein the five-bar linkage is composed primarily of aluminum having a high stiffness-to-mass ratio and comprises a parallelogram linkage with one vertex coupled to one end of a fifth link, the other end of said fifth link being coupled to a limb coupling cuff via a joint allowing limb rotation out of the plane of said parallelogram.
5. The system of claim 4 wherein said fifth link is L-shaped to accommodate limb movements.
6. The system of claim 1 wherein said torque is proportional to the angular velocity of said rotation.
7. The system of claim 6 wherein proportionality constants may be varied for each person using the system.
8. A method of restraining limb motion comprising the steps of:
   a) coupling a limb to an N degree of freedom linkage mechanism having a plurality of rotational joints which permit rotation of said limb about different axes where N is at least two;
   b) sensing a parameter of said movement of a predetermined one or more of said joints; and
   c) applying a resistive torque that is responsive to the angular velocity of rotation to said predetermined subset of said joints such that said torque is a function of the angular velocity of said rotation.
9. A method of restraining limb motion, as recited in claim 8, in which N is at least 3.
10. A method of restraining limb motion, as recited in claim 8, in which the linkage mechanism further comprises a five-bar linkage.
11. A method of restraining limb motion, as recited in claim 10, in which the five-bar linkage is composed primarily of aluminum having a high stiffness-to-mass ratio and comprises a parallelogram linkage with one vertex coupled to one end of a fifth link, the other end of said fifth link being coupled to a limb coupling cuff via a joint allowing limb rotation out of the plane of said parallelogram.

12. A method of restraining limb motion, as recited in claim 11, in which said fifth link is L-shaped to accommodate limb movements.

13. A method of restraining limb motion, as recited in claim 8, in which said torque is proportional to the angular velocity of said rotation.

14. A method of restraining limb motion, as recited in claim 13, in which a constant of proportionality can be varied for each person using the method.

15. An apparatus to restrain limb motion comprising:
a linkage mechanism having a plurality of rotational joints;
a mounting plate coupled to said linkage mechanism, said mounting plate being attached to an external surface for supporting said linkage mechanism;
a limb coupling assembly for supporting a forearm of a user, said limb coupling assembly connected to said linkage mechanism such that the forearm can be moved in a horizontal plane and tilted about an axis in that horizontal plane;
a sensor for detecting the angular velocity of rotation of said joints; and
a brake responsive to said angular velocity of rotation for applying a resistive torque to said joints.

16. An apparatus to restrain limb motion comprising:
a linkage mechanism having at least four joints, such that said joints are interconnected by rigid links;
a mounting plate coupled to said linkage mechanism, said mounting plate being attached to an external surface for supporting said linkage mechanism;
a limb coupling assembly for supporting a forearm, said limb coupling assembly connected to said linkage mechanism such that the forearm can be moved in a horizontal plane and tilted about an axis in that horizontal plane;
a plurality of sensors for detecting the angle of each joint and producing output signal in accordance with said angle;
an apparatus for calculating the angular velocity of said joints from said sensor output signal;
a plurality of particle brakes responsive to said output signal(s) for applying a resistive torque to said joints.

17. A system to restrain limb motion comprising:
a) an N degree of freedom linkage mechanism having a plurality of rotational joints for coupling said limb thereto which permits movement of said limb about N different axes where N is at least two;
b) sensor means coupled to a predetermined one or more of said joints for generating a signal proportional to a parameter of said movement; and
c) braking means responsive to the signal for applying a resistive force to a predetermined one or more of said joints and wherein said force is a function of the movement parameter.

18. A method of restraining limb motion comprising the steps of:
a) coupling a limb to an N degree of freedom linkage mechanism having a plurality of joints which permit movement of said limb about different axes where N is at least two;
b) sensing a parameter of said movement of a predetermined one or more of said joints; and
c) applying a resistive force that is responsive to the sensed parameter to said predetermined joints such that said force is a function of the sensed parameter.

19. An apparatus to restrain limb motion comprising:
a linkage mechanism having a plurality of joints;
a mounting plate coupled to said linkage mechanism, said mounting plate being attached to an external surface for supporting said linkage mechanism;
a limb coupling assembly for supporting a forearm, said limb coupling assembly connected to said linkage mechanism such that the forearm can be moved in a horizontal plane and tilted about an axis in that horizontal plane;
a sensor for detecting motion of said joints; and
a brake responsive to the sensed motion for applying a resistive force to said joints.

20. An apparatus to restrain limb motion comprising:
a linkage mechanism having at least four joints, such that said joints are interconnected by rigid links;
a mounting plate coupled to said linkage mechanism, said mounting plate being attached to an external surface for supporting said linkage mechanism;
a limb coupling assembly for supporting a forearm, said limb coupling assembly connected to said linkage mechanism such that the forearm can be moved in a horizontal plane and tilted about said horizontal plane;
a plurality of sensors detecting movement of each joint and producing an output signal in accordance with said movement;
a plurality of particle brakes responsive to the sensed movement for applying a resistive force to said joints.

* * * * *